(12) United States Patent
Iyer

(10) Patent No.: US 9,009,935 B2
(45) Date of Patent: Apr. 21, 2015

(54) METHODS TO PREVENT HIGH VOLTAGE ARCING UNDER CAPACITORS USED IN FILTERED FEEDTHROUGHS

(75) Inventor: Rajesh V. Iyer, Eden Prairie, MN (US)

(73) Assignee: Medtronic, Inc., Minneapolis, MN (US)

( * ) Notice: Subject to any disclaimer, the term of this patent is extended or adjusted under 35 U.S.C. 154(b) by 617 days.

(21) Appl. No.: 12/436,392

(22) Filed: May 6, 2009

(65) Prior Publication Data
US 2010/0284124 A1  Nov. 11, 2010

(51) Int. Cl.
*H01G 7/00* (2006.01)
*H01G 4/35* (2006.01)
*H01G 2/10* (2006.01)
*H01G 4/236* (2006.01)
*A61N 1/375* (2006.01)

(52) U.S. Cl.
CPC ............... *H01G 4/35* (2013.01); *A61N 1/3754* (2013.01); *H01G 2/106* (2013.01); *H01G 4/236* (2013.01)

(58) Field of Classification Search
CPC .............................. H01G 2/106; H01G 4/242
USPC ........... 29/25.35–25.42, 592.1, 867; 361/302, 361/307; 333/182; 607/37
See application file for complete search history.

(56) References Cited

U.S. PATENT DOCUMENTS

| | | | |
|---|---|---|---|
| 3,646,405 A | 2/1972 | Wallis et al. | |
| 3,803,875 A | 4/1974 | Root et al. | |
| 3,920,888 A | 11/1975 | Barr | |
| 4,152,540 A | 5/1979 | Duncan et al. | |
| 4,285,730 A | 8/1981 | Sanford et al. | |
| 4,314,031 A | 2/1982 | Sanford et al. | |
| 4,323,654 A | 4/1982 | Tick et al. | |
| 4,420,569 A | 12/1983 | Tick | |
| 4,421,947 A | 12/1983 | Kyle | |
| 4,424,551 A | 1/1984 | Stevenson et al. | |
| 4,940,858 A | 7/1990 | Taylor et al. | |
| 4,943,686 A | 7/1990 | Kucharek | |
| 5,015,530 A | 5/1991 | Brow et al. | |
| 5,021,307 A | 6/1991 | Brow et al. | |
| 5,089,446 A | 2/1992 | Cornelius et al. | |
| 5,104,738 A | 4/1992 | Brow et al. | |
| 5,104,755 A | 4/1992 | Taylor et al. | |
| 5,175,067 A | 12/1992 | Taylor et al. | |
| 5,294,241 A | 3/1994 | Taylor et al. | |
| 5,306,581 A | 4/1994 | Taylor et al. | |

(Continued)

FOREIGN PATENT DOCUMENTS

DE  8631853 U1  11/1988
EP  0404435 A1  12/1990

(Continued)

OTHER PUBLICATIONS (PCT/US10/033810) PCT Invitation to Pay Additional Fees and Partial Search Report.

(Continued)

*Primary Examiner* — Minh Trinh
(74) *Attorney, Agent, or Firm* — Carol F. Barry

(57) ABSTRACT

A capacitor assembly for use in, and a method of assembling, a filtered feedthrough. The capacitor includes an insulative member fixedly attached to its bottom portion to inhibit high voltage arcing. The termination material present on the inner and outer diameters of the capacitor is absent from a portion of the capacitor proximate the bottom portion, e.g., at the insulative member.

17 Claims, 9 Drawing Sheets

(56) References Cited

U.S. PATENT DOCUMENTS

| | | | |
|---|---|---|---|
| 5,333,095 A * | 7/1994 | Stevenson et al. | 361/302 |
| 5,648,302 A | 7/1997 | Brow et al. | |
| 5,650,759 A | 7/1997 | Hittman et al. | |
| 5,693,580 A | 12/1997 | Brow et al. | |
| 5,817,984 A | 10/1998 | Taylor et al. | |
| 5,821,011 A | 10/1998 | Taylor et al. | |
| 5,825,608 A | 10/1998 | Duva et al. | |
| 5,851,222 A | 12/1998 | Taylor et al. | |
| 5,866,851 A | 2/1999 | Taylor et al. | |
| 5,867,361 A | 2/1999 | Wolf et al. | |
| 5,870,272 A | 2/1999 | Seifried et al. | |
| 5,871,513 A | 2/1999 | Taylor et al. | |
| 5,902,326 A | 5/1999 | Lessar et al. | |
| 5,905,627 A * | 5/1999 | Brendel et al. | 361/302 |
| 6,031,710 A * | 2/2000 | Wolf et al. | 361/302 |
| 6,076,017 A | 6/2000 | Taylor et al. | |
| 6,090,503 A | 7/2000 | Taylor et al. | |
| 6,275,369 B1 | 8/2001 | Stevenson et al. | |
| 6,349,025 B1 | 2/2002 | Fraley et al. | |
| 6,453,551 B1 * | 9/2002 | Nordquist et al. | 29/862 |
| 6,536,882 B1 | 3/2003 | Hawkins et al. | |
| 6,566,978 B2 | 5/2003 | Stevenson et al. | |
| 6,603,182 B1 | 8/2003 | Low et al. | |
| 6,643,903 B2 | 11/2003 | Stevenson et al. | |
| 6,660,116 B2 | 12/2003 | Wolf et al. | |
| 6,759,163 B2 | 7/2004 | Frysz et al. | |
| 6,759,309 B2 | 7/2004 | Gross | |
| 6,768,629 B1 | 7/2004 | Allen et al. | |
| 6,855,456 B2 | 2/2005 | Taylor et al. | |
| 6,888,233 B2 | 5/2005 | Horning et al. | |
| 6,924,165 B2 | 8/2005 | Horning et al. | |
| 7,035,077 B2 * | 4/2006 | Brendel | 361/302 |
| 7,046,499 B1 | 5/2006 | Imani et al. | |
| 7,094,967 B2 | 8/2006 | Evans et al. | |
| 7,098,117 B2 | 8/2006 | Najafi et al. | |
| 7,210,966 B2 | 5/2007 | Taylor et | |
| 7,214,441 B2 | 5/2007 | Cortright et al. | |
| 7,260,434 B1 | 8/2007 | Lim et al. | |
| 7,281,305 B1 | 10/2007 | Iyer et al. | |
| 7,285,509 B2 | 10/2007 | Bayya et al. | |
| 7,916,448 B2 * | 3/2011 | Zhao et al. | 361/307 |
| 8,373,965 B2 * | 2/2013 | Iyer | 361/302 |
| 2001/0050837 A1 | 12/2001 | Stevenson et al. | |
| 2003/0083715 A1 | 5/2003 | Taylor et al. | |
| 2003/0123215 A1 | 7/2003 | Allen et al. | |
| 2003/0125185 A1 | 7/2003 | Hirose | |
| 2003/0179536 A1 | 9/2003 | Stevenson et al. | |
| 2004/0126953 A1 | 7/2004 | Cheung | |
| 2004/0152229 A1 | 8/2004 | Najafi et al. | |
| 2004/0180464 A1 | 9/2004 | Horning et al. | |
| 2004/0244484 A1 | 12/2004 | Horning et al. | |
| 2005/0060003 A1 | 3/2005 | Taylor et al. | |
| 2005/0092507 A1 | 5/2005 | Marshall et al. | |
| 2005/0186823 A1 | 8/2005 | Ring et al. | |
| 2006/0009813 A1 | 1/2006 | Taylor et al. | |
| 2006/0173506 A1 | 8/2006 | Rusin et al. | |
| 2006/0192272 A1 | 8/2006 | Receveur et al. | |
| 2006/0247714 A1 | 11/2006 | Taylor et al. | |
| 2006/0290257 A1 | 12/2006 | Heo et al. | |
| 2007/0004580 A1 | 1/2007 | Kass | |
| 2007/0179554 A1 | 8/2007 | Iyer et al. | |
| 2007/0179555 A1 | 8/2007 | Iyer et al. | |
| 2007/0217121 A1 | 9/2007 | Fu et al. | |
| 2007/0234540 A1 | 10/2007 | Iyer et al. | |
| 2007/0239223 A1 | 10/2007 | Engmark et al. | |
| 2007/0260282 A1 | 11/2007 | Taylor et al. | |
| 2008/0060844 A1 | 3/2008 | Teske et al. | |
| 2008/0118831 A1 | 5/2008 | Jouanneau-Si-Larbi et al. | |
| 2009/0079517 A1 | 3/2009 | Iyer | |
| 2009/0079518 A1 | 3/2009 | Iyer | |
| 2009/0079519 A1 | 3/2009 | Iyer | |

FOREIGN PATENT DOCUMENTS

| | | |
|---|---|---|
| EP | 0404435 B1 | 9/1996 |
| WO | WO 2007/117942 | 10/2007 |

OTHER PUBLICATIONS

DIEMAT DM2995PF Series Lead (Pb)-Free Sealing Glass Preforms—Preliminary Data Sheet, Aug. 27, 2006, 4 pages.
DIEMAT DM2700PF Series, DM2700PF/DM2760PF, Low-Temperature Sealing Glass Preforms—Product Data Sheet, Jul. 24, 2006, 4 pages.
DIEMAT, Inc. Material Safety Data Sheet—DM2995PF, Aug. 23, 2006, 4 pages.
International Search Report for PCT/US2009/050191 dated Oct. 6, 2009, 4 pages.
International Search Report for PCT/US2008/077179 dated May 25, 2009, 4 pages.
Yourassowsky, E. et al., Combination of minocycline and rifampicin against methicillin- and gentamicin-resistant *Staphylococcus aureus*, J Clin Pathol 1981; 34:559-563.
Bayston, R. et al., Antimicrobial activity of silicone rubber used in hydrocephalus shunts, after impregnation with antimicrobial substances, J Clin Pathol 1981; 34:1057-1062.

\* cited by examiner

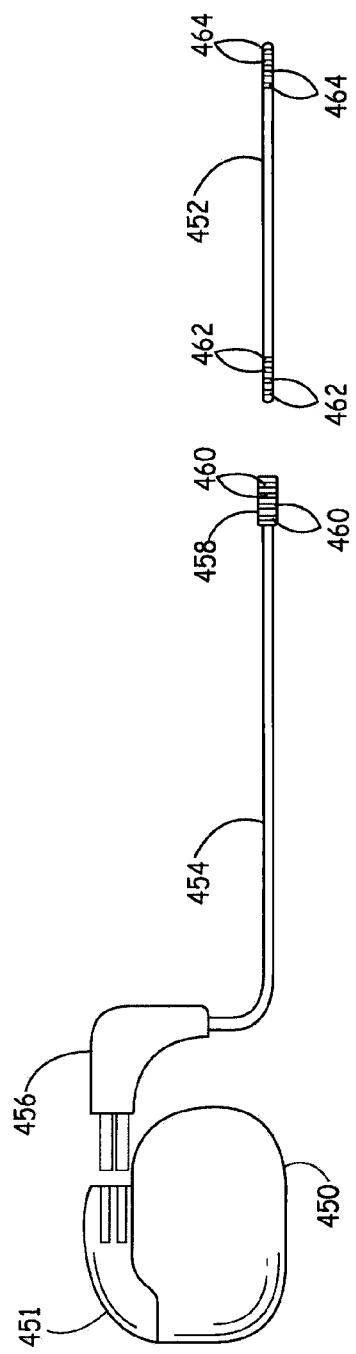
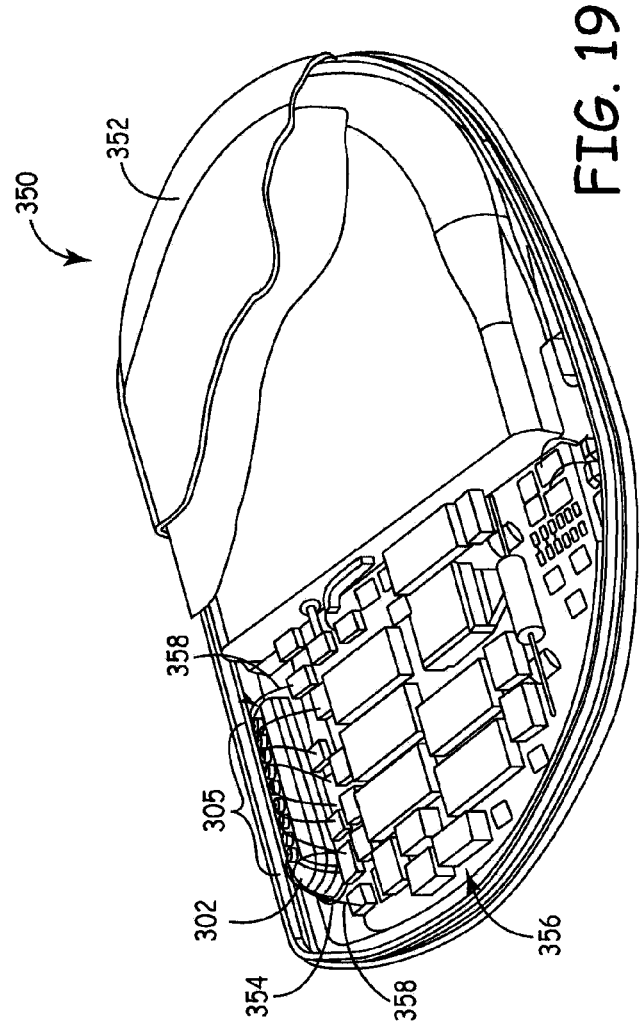

METHODS TO PREVENT HIGH VOLTAGE ARCING UNDER CAPACITORS USED IN FILTERED FEEDTHROUGHS

FIELD

The present disclosure relates to a capacitor assembly and associated method of assembling a filtered feedthrough for implantable medical devices and, more particularly, to a method in which a capacitor assembly that inhibits high voltage arcing is utilized.

INTRODUCTION

The background description provided herein is for the purpose of generally presenting the context of the disclosure. Work of the presently named inventors, to the extent the work is described in this background section, as well as aspects of the description that may not otherwise qualify as prior art at the time of filing, are neither expressly nor impliedly admitted as prior art against the present disclosure.

Electrical feedthroughs serve the purpose of providing an electrical circuit path extending from the interior of a hermetically sealed container to an external point outside the container. A conductive path is provided through the feedthrough by a conductor pin which is electrically insulated from the container. Many feedthroughs are known in the art that provide the electrical path and seal the electrical container from its ambient environment. Such feedthroughs typically include a ferrule, the conductor pin or lead and a hermetic ceramic seal which supports the pin within the ferrule. Such feedthroughs are typically used in electrical medical devices such as implantable pulse generators (IPGs). It is known that such electrical devices can, under some circumstances, be susceptible to electromagnetic interference (EMI). At certain frequencies for example, EMI can inhibit pacing in an IPG. This problem has been addressed by incorporating a capacitor structure within the feedthrough ferrule, thus shunting any EMI at the entrance to the IPG for high frequencies. This has been accomplished with the aforementioned capacitor device by combining it with the feedthrough and incorporating it directly into the feedthrough ferrule. Typically, the capacitor electrically contacts the pin lead and the ferrule.

Many different insulator structures and related mounting methods are known in the art for use in medical devices wherein the insulator structure also provides a hermetic seal to prevent entry of body fluids into the housing of the medical device. The feedthrough terminal pins, however, are connected to one or more lead wires which effectively act as an antenna and thus tend to collect stray or electromagnetic interference (EMI) signals for transmission to the interior of the medical device. In some prior art devices, ceramic chip capacitors are added to the internal electronics to filter and thus control the effects of such interference signals. This internal, so-called "on-board" filtering technique has potentially serious disadvantages due to intrinsic parasitic resonances of the chip capacitors and EMI radiation entering the interior of the device housing.

In another approach, a filter capacitor is combined directly with a terminal pin assembly to decouple interference signals to the housing of the medical device. In a typical construction, a coaxial feedthrough filter capacitor is connected to a feedthrough assembly to suppress and decouple undesired interference or noise transmission along a terminal pin.

So-called discoidal capacitors having two sets of electrode plates embedded in spaced relation within an insulative substrate or base typically form a ceramic monolith in such capacitors. One set of the electrode plates is electrically connected at an inner diameter surface, e.g., with a termination material, of the discoidal structure to the conductive terminal pin utilized to pass the desired electrical signal or signals. The other or second set of electrode plates is coupled, e.g., with a termination material, at an outer diameter surface of the discoidal capacitor to a cylindrical ferrule of conductive material, wherein the ferrule is electrically connected in turn to the conductive housing or case of the electronic instrument.

In operation, the discoidal capacitor permits passage of relatively low frequency electrical signals along the terminal pin, while shunting and shielding undesired interference signals of typically high frequency to the conductive housing. Feedthrough capacitors of this general type are commonly employed in implantable pacemakers, defibrillators and the like, wherein a device housing is constructed from a conductive biocompatible metal such as titanium and is electrically coupled to the feedthrough filter capacitor. The filter capacitor and terminal pin assembly prevent interference signals from entering the interior of the device housing, where such interference signals might otherwise adversely affect a desired function such as pacing or defibrillating.

In the past, feedthrough filter capacitors for heart pacemakers and the like have typically been constructed by preassembly of the discoidal capacitor with a terminal pin subassembly which includes the conductive terminal pin and ferrule. More specifically, the terminal pin subassembly is prefabricated to include one or more conductive terminal pins supported within the conductive ferrule by means of a hermetically sealed insulator ring or bead. See, for example, the terminal pin subassemblies disclosed in U.S. Pat. Nos. 3,920,888, 4,152,540; 4,421,947; and 4,424,551. The terminal pin subassembly thus defines a small annular space or gap disposed radially between the inner terminal pin and the outer ferrule. A small discoidal capacitor of appropriate size and shape is then installed into this annular space or gap, in conductive relation with the terminal pin and ferrule, e.g., by means of soldering or conductive adhesive. The thus-constructed feedthrough capacitor assembly is then mounted within an opening in the pacemaker housing, with the conductive ferrule in electrical and hermetically sealed relation in respect of the housing, shield or container of the medical device.

Although feedthrough filter capacitor assemblies of the type described above have performed in a generally satisfactory manner, such filter capacitor assemblies may be susceptible to high voltage arcing between the inner diameter and outer diameter of the capacitor, particularly along the bottom of the capacitor.

The present teachings provide a feedthrough filter capacitor assembly of the type used, for example, in implantable medical devices such as heart pacemakers and the like, wherein the filter capacitor is designed to inhibit high voltage arcing along the bottom of the capacitor.

SUMMARY

In various exemplary embodiments, the present disclosure relates to a method of assembling a filtered feedthrough assembly. The method includes providing a capacitor having a top portion, a bottom portion, an outer diameter portion and an inner diameter portion. The inner diameter portion defines at least one aperture extending from the top portion to the bottom portion. An insulative member is fixedly attached to the bottom portion of the capacitor and is configured to inhibit high voltage arcing. The method includes inserting at least one terminal pin within a ferrule and fixedly securing the capacitor with attached insulative member within the ferrule, wherein the at least one terminal pin extends through the opening and extends through the at least one aperture.

In further various exemplary embodiments, the present disclosure relates to a capacitor assembly for use in a filtered feedthrough for an implantable medical device. The capacitor assembly includes a capacitor having a top portion, a bottom portion, an outer diameter portion and an inner diameter portion, wherein the inner diameter portion defines at least one aperture extending from the top portion to the bottom portion. The capacitor includes a plurality of conductive plates. An outer diameter termination material is applied to the outer diameter portion of the capacitor and electrically couples a first subset of the plurality of conductive plates. The outer diameter termination material is absent from an outer diameter lower portion of the outer diameter portion adjacent the bottom portion of the capacitor. An inner diameter termination material is applied to the inner diameter portion of the capacitor and electrically couples a second subset of the plurality of conductive plates. The inner diameter termination material is absent from an inner diameter lower portion of the inner diameter portion adjacent the bottom portion of the capacitor.

In further various exemplary embodiments, the present disclosure relates to a method of assembling a filtered feedthrough assembly. The method includes providing a capacitor having a top portion, a bottom portion, an outer diameter portion and an inner diameter portion. The inner diameter portion defines at least one aperture extending from the top portion to the bottom portion. The capacitor includes a plurality of conductive plates. An outer diameter termination material on the outer diameter portion of the capacitor electrically couples a first subset of the plurality of conductive plates. The outer diameter termination material is absent from an outer diameter lower portion of the outer diameter portion adjacent the bottom portion of the capacitor. An inner diameter termination material on the inner diameter portion of the capacitor electrically couples a second subset of the plurality of conductive plates. The inner diameter termination material is absent from an inner diameter lower portion of the inner diameter portion adjacent the bottom portion of the capacitor. The method includes inserting at least one terminal pin within a ferrule and fixedly securing the capacitor with attached insulative member within the ferrule, wherein the at least one terminal pin extends through the opening and extends through the at least one aperture.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF DRAWINGS

The present disclosure will become more fully understood from the detailed description and the accompanying drawings, wherein:

FIG. 18 is a perspective view of a partially disassembled implantable medical device; and FIG. 19 is an isometric cutaway view of an implantable medical device incorporating the multipolar (multiple pin) filtered feedthrough assembly of FIG. 17.

DESCRIPTION

Figure 1:
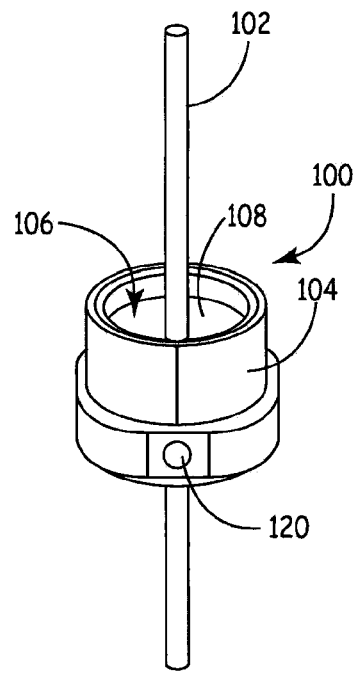
FIGS. 1 and 2 are isometric and cross-sectional views, respectively, of a known unipolar (single pin) feedthrough assembly prior to attachment of a discrete discoidal capacitor.

The following description is merely exemplary in nature and is in no way intended to limit the disclosure, its application, or uses. For purposes of clarity, the same reference numbers will be used in the drawings to identify similar elements. As used herein, the phrase at least one of A, B, and C should be construed to mean a logical (A or B or C), using a non-exclusive logical or. It should be understood that steps within a method can be executed in different order without altering the principles of the present disclosure.

Figure 2:
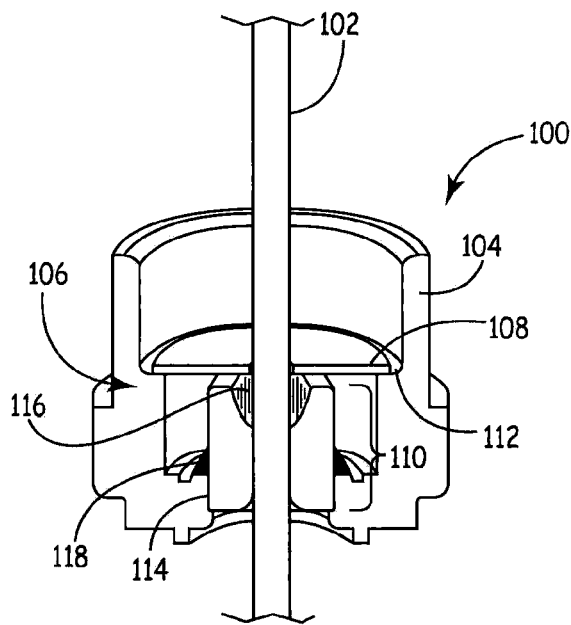

FIGS. 1 and 2 are isometric and cross-sectional views, respectively, of a known unipolar (single pin) feedthrough assembly 100 having a terminal pin 102 extending therethrough. Assembly 100 comprises a generally cylindrical ferrule 104 having a cavity through which pin 102 passes. Ferrule 104 is made of an electrically conductive material (e.g., titanium alloy) and is configured to be fixedly coupled (e.g., welded) to the container of a medical device as described below in conjunction with FIGS. 18-19. An insulating structure 106 is disposed within ferrule 104 to secure pin 102 relative to ferrule 104 and to electrically isolate pin 102 from ferrule 104. Insulating structure 106 comprises a supporting structure 108 and a joint-insulator sub-assembly 110, both of which are disposed around terminal pin 102. As will be more fully described below, joint-insulator sub-assembly 110 acts as an insulative seal and can take the form of, for example, a braze joint. Supporting structure 108 is made of a non-conductive material (e.g., polyimide) and rests on an inner ledge 112 provided within ferrule 104. As will be seen in FIG. 3, a discrete discoidal capacitor 150 can be threaded over terminal pin 102 and fixedly coupled to supporting structure 108 to attach the capacitor to feedthrough assembly 100.

As can be seen in FIG. 2, braze joint 110 comprises three main components: an insulator ring 114 (e.g., made from a ceramic material) that insulates pin 102 from ferrule 104, a pin-insulator braze 116 (e.g., made from gold) that couples insulating ring 114 to pin 102, and an insulator-ferrule braze 118 (e.g., made from gold) that couples insulating ring 114 to ferrule 104. Braze joint 110 is exposed along the underside of ferrule 104. When ferrule 104 is fixedly coupled to the container of the medical device, the lower portion of ferrule 104, and thus the lower portion of braze joint 110, can be exposed to body fluids. For this reason, it is important that braze joint 110 forms a hermetic seal between ferrule 104 and terminal pin 102. Braze joint 110 can be leak tested. To permit this test to be performed, an aperture 120 (FIG. 1) is provided through ferrule 104 to the inner annular cavity formed by the outer surface of braze joint 110, the lower surface of supporting structure 108, and the inner surface of ferrule 104. A gas is delivered through aperture 120 into the inner annular cavity, and aperture 120 is plugged. Preferably, a gas of low molecular weight (e.g., helium or hydrogen) is chosen so that it can easily penetrate small cracks in braze joint 110. Feedthrough 100 is then monitored for the presence of the gas proximate braze joint 110 by way of, for example, a mass spectrometer. If no gas is detected, it is concluded that braze joint 110 has formed a satisfactory seal.

Figure 3:
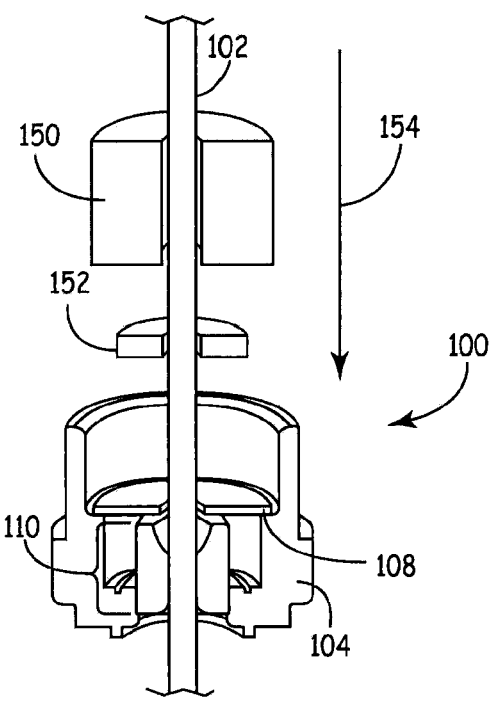
FIGS. 3-5 illustrate a prior art method of attaching a discrete discoidal capacitor to the feedthrough assembly shown in FIGS. 1 and 2.
Figure 4:
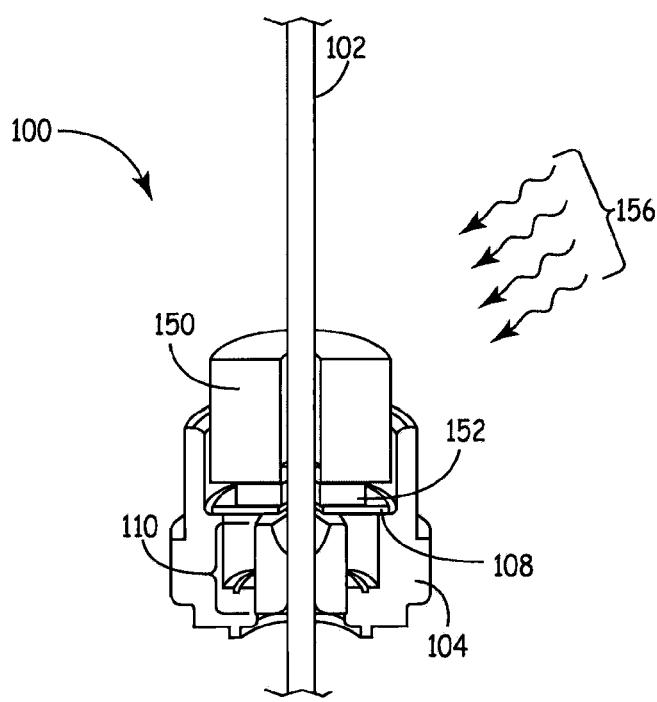
Figure 5:
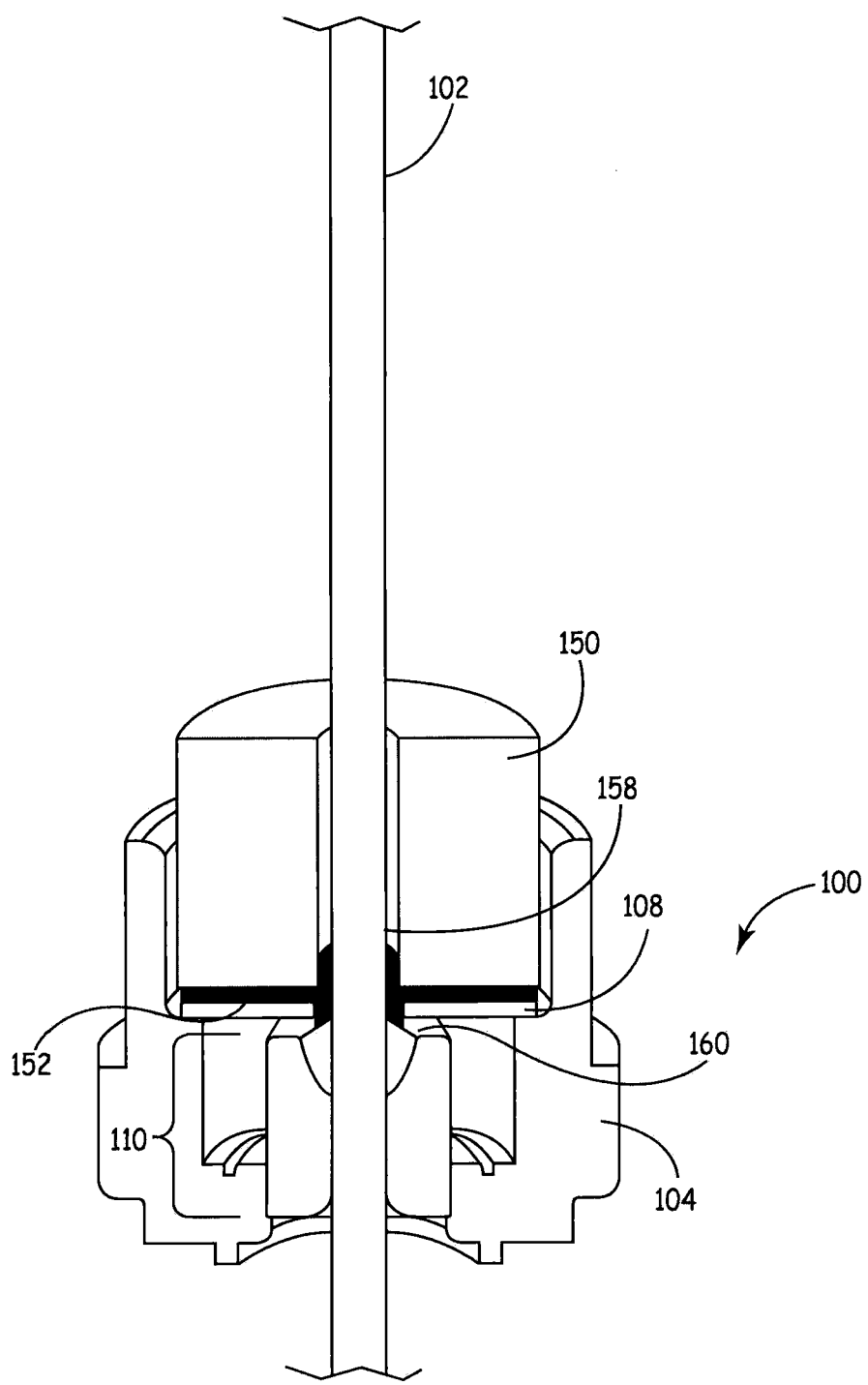

Terminal pin 102 provides a conductive path from the interior of a medical device (not shown) to one or more lead wires exterior to the medical device. As described previously, these lead wires are known to act as antennae that collect stray electromagnetic interference (EMI) signals, which can interfere with the proper operation of the device. To suppress and/or transfer such EMI signals to the container of the medical device, a discrete discoidal capacitor can be attached to feedthrough assembly 100. In particular, the capacitor can be disposed around and electrically coupled to terminal pin 102 and fixedly coupled to supporting structure 108. FIGS. 3-5 illustrate a known manner of attaching a discrete discoidal capacitor 150 to feedthrough assembly 100 shown in FIGS. 1 and 2. The attachment method commences as a ring-shaped preform 152 of non-conductive epoxy is threaded over terminal pin 102 (indicated in FIG. 3 by arrow 154). Capacitor 150 is then threaded over pin 102 and positioned against preform 152 such that preform 152 is sandwiched between capacitor 150 and supporting structure 108. Next, feedthrough assembly 100 is placed within a curing oven and heated to a predetermined temperature (e.g., approximately 175 degrees Celsius) to thermally cure preform 152 (indicated in FIG. 4 by arrows 156) and thus physically couple capacitor 150 to supporting structure 108.

During curing, preform 152 melts and disperses under the weight of capacitor 150, which moves downward toward supporting structure 108. Preform 152 disperses along the annular space provided between the bottom surface of capacitor 150 and the upper surface of supporting structure 108 to physically couple capacitor 150 and supporting structure 108 as described above. In addition, preform 152 can disperse upward into the annular space provided between the inner surface of capacitor 150 and outer surface of terminal pin 102 (shown in FIG. 5 at 158). Dispersal of preform 152 in this manner can interfere with the proper electrical coupling of capacitor 150 to terminal pin 102. Also, during curing, preform 152 can disperse downward into insulating structure 110 (shown in FIG. 5 at 160). This dispersal can result in preform 152 covering any cracks that have formed through braze joint 110 and, consequently, prevent the accurate leak testing of feedthrough assembly 100.

Arcing between the inner surface and outer surface of the capacitor 150 can occur (for example, along the bottom surface of the capacitor 150) in the presence of the high voltage associated with the feedthrough assembly 100. In addition to the limitations associated with utilizing epoxy preforms 152 described above, epoxy preforms 152 can be ineffective for inhibiting this high voltage surface arcing along the bottom of the capacitor 150. The epoxy preform 152 tends to outgas and have excessive weight loss when subjected to the heat treatment associated with electrically connecting the terminal pin 102 with the inner surface and the ferrule 104 with the outer surface of the capacitor 150, e.g., with high-temperature solder.

Figure 6:
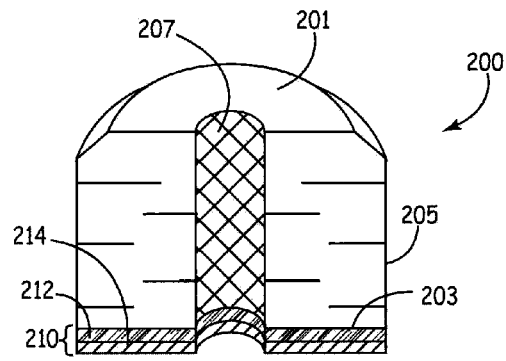
FIGS. 6-13 are cross-sectional views of a discrete discoidal capacitor with a fixedly attached insulative member for use in a unipolar (single pin) filtered feedthrough assembly according to various exemplary embodiments of the present disclosure.

Referring now to FIG. 6, a cross-sectional view of a capacitor 200 that inhibits surface arcing according to various exemplary embodiments of the present disclosure is illustrated. The capacitor 200 includes a top portion 201, a bottom portion 203, an outside diameter portion 205 and an inner diameter portion 207. Fixedly attached to the bottom portion 203 of capacitor 200 is an insulative member 210. The insulative member 210 illustrated in FIG. 6 includes an adhesive 212 and a base member 214. The adhesive 212 adheres or otherwise attaches the base member 214 to the bottom portion 203 of the capacitor 200. The adhesive 212 can be, for example, a glass material, a polyimide material, or a combination of one or more of these materials. The base member 214 can be made of a ceramic material (such as a low temperature co-fired ceramic ("LTCC") or alumina), a plastic material (such as polyaryletheretherketone ("PEEK")), a polyimide material, a glass material, or a combination of one or more of these materials. Insulative member 210 essentially bonds with the bottom portion 203 of the capacitor 200 to form a unitary structure. Insulative member 210 inhibits high voltage arcing along the bottom portion 203 of the capacitor, for example, by increasing the length of the surface that an arc must travel between inner diameter portion 207 and outer diameter portion 205, as well as preventing a direct line of sight between the terminal pin 102 and ferrule 104.

Figure 7:
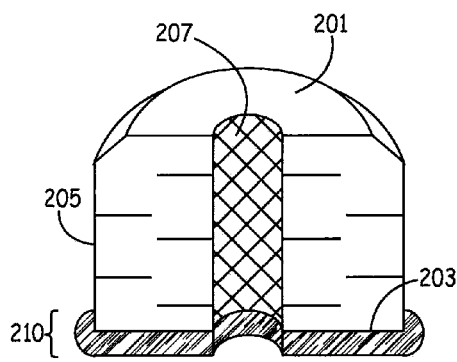

In the exemplary embodiment illustrated in FIG. 7, capacitor 200 includes an insulative member 210 that substantially covers the entire surface area of the bottom portion 203 of the capacitor 200 and extends around the radius and into contact with the outer diameter 205 of the capacitor 200. Insulative member 210 can be an insulative coating, e.g., made of a non-conductive epoxy, a glass material, a plastic material, a polyimide material, or a combination of one or more of these materials. Furthermore, the insulative member 210 shown in FIG. 7 can include a base member adhered to the bottom portion 203, similar to that illustrated in FIG. 6, in which the base member extends around the radius and into contact with the outer diameter 205 of the capacitor 200.

Figure 8:
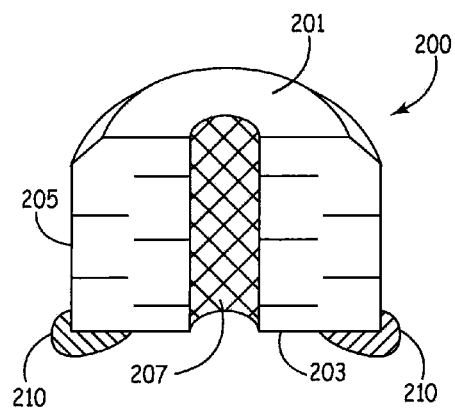

In the exemplary embodiment illustrated in FIG. 8, capacitor 200 includes an insulative member 210 that covers only a portion of the surface area of the bottom portion 203 of the capacitor 200 and extends around the radius and into contact with the outer diameter 205 of the capacitor 200. Insulative member 210 can be an insulative coating, e.g., made of a glass material, a polyimide material, or a combination of one or more of these materials. Furthermore, the insulative member 210 shown in FIG. 8 can include a base member adhered to the bottom portion 203, similar to that illustrated in FIG. 6, in which the base member extends around the radius and into contact with the outer diameter 205 of the capacitor 200.

Figure 9:
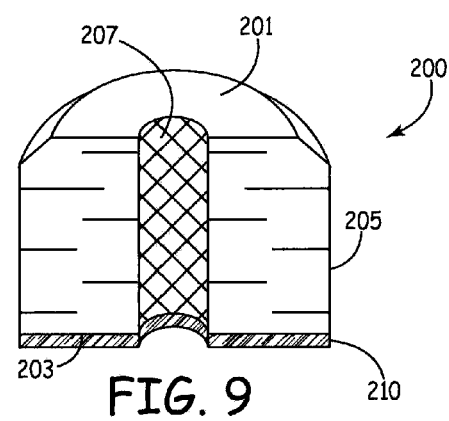

In additional exemplary embodiments of the present disclosure, a capacitor 200 includes an insulative member 210 that substantially covers the entire surface area of the bottom portion 203 of the capacitor 200, as shown in FIG. 9. Insulative member 210 can be an insulative coating, e.g., made of a glass material, a plastic material, a polyimide material, or a combination of one or more of these materials.

Figure 10:
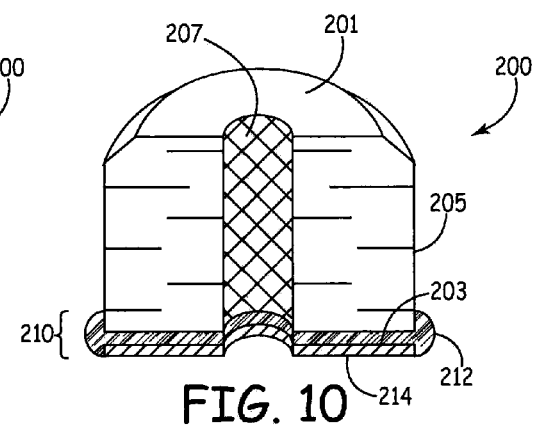

Referring now to FIG. 10, a cross-sectional view of a capacitor 200 that inhibits surface arcing according to various exemplary embodiments of the present disclosure is illustrated. The capacitor 200 includes a top portion 201, a bottom portion 203, an outside diameter portion 205 and an inner diameter portion 207. Fixedly attached to the bottom portion 203 of capacitor 200 is an insulative member 210. The insulative member 210 illustrated in FIG. 10 includes an adhesive 212 and a base member 214. The adhesive 212 adheres or otherwise attaches the base member 214 to the bottom portion 203 of the capacitor 200. The adhesive 212 can be, for example, a glass material, a polyimide material, or a combination of one or more of these materials. The base member 214 can be made of an alumina material, a plastic material, a polyimide material, a glass material, a ceramic material, or a combination of one or more of these materials. Insulative member 210 essentially bonds with the bottom portion 203 of the capacitor 200 to form a unitary structure. Insulative member 210 substantially covers the entire surface area of the bottom portion 203 of the capacitor 200 and extends around the radius and into contact with the outer diameter 205 of the capacitor 200. The portion that extends into contact with the bottom portion 203 of the capacitor 200 can be the adhesive 212, as shown in FIG. 10, or the base member 214 (not shown). Insulative member 210 inhibits high voltage arcing along the bottom portion 203 of the capacitor, for example, by increasing the length of the surface that an arc must travel between inner diameter portion 207 and outer diameter portion 205, as well as preventing a direct line of sight between the terminal pin 102 and ferrule 104.

Figure 11:
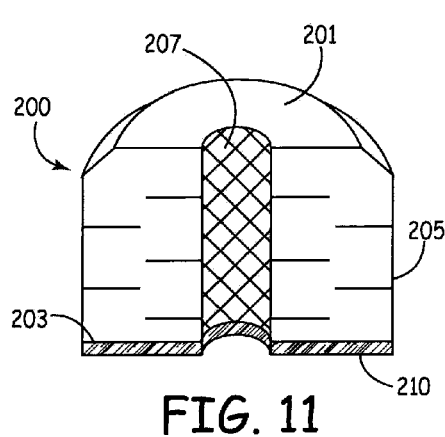

Referring now to FIG. 11, a cross-sectional view of a capacitor 200 that inhibits surface arcing according to additional exemplary embodiments of the present disclosure is illustrated. The insulative member 210 shown in FIG. 11 can comprise a base member that is fixedly attached to the bottom portion 203 of the capacitor 200. For example, the insulative member 210 can comprise a low temperature co-fired ceramic ("LTCC") material that is laminated to the bottom portion 203 of capacitor 200. It is contemplated that other insulative members 210, such as those made of an alumina material, a plastic material, a polyimide material, a glass material, a ceramic material, or a combination of one or more of these materials, can be utilized. Furthermore, the insulative member 210 can be fixedly attached to the bottom portion 203 of the capacitor 200 by materials and/or processes other than lamination, such as a glass material, a polyimide material, or a combination of one or more of these materials. One of the benefits associated with utilizing a separate insulative member 210 fixedly attached to the capacitor 200 is that the insulative layer is substantially uniform across the surface area of the bottom portion 203.

Figure 12:
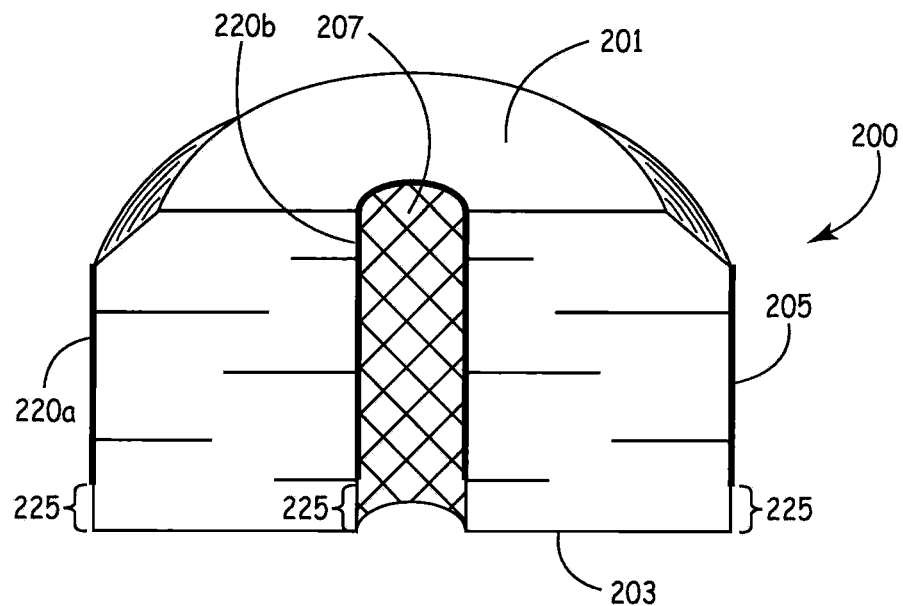

In further additional exemplary embodiments of the present disclosure, a capacitor 200 can have an unterminated portion 225 on one of or each of the outer diameter and inner diameter portions 205, 207 proximate to the bottom portion 203 of the capacitor 200, as illustrated in FIG. 12. The outer and inner diameter portions 205, 207 of capacitor 200 are coated with a conductive termination material 220a and 220b, respectively. Termination material 220a electrically couples one of the two sets of the electrode plates that form the capacitor with the outer diameter portion 205. Termination material 220b electrically couples the other one of the two sets of the electrode plates that form the capacitor with the inner diameter portion 207. In a typical capacitor, the termination material extends along the full length of the inner and outer diameter portions of the capacitor 200. The exemplary capacitor 200 illustrated in FIG. 12 includes unterminated portions 225 on each of the outer diameter and inner diameter portions 205, 207 proximate to the bottom portion 203, although only one of the inner and outer diameter portions including an unterminated portion is within the scope of the present disclosure. In this construction, capacitor 200 inhibits high voltage arcing along the bottom portion 203 of the capacitor, for example, by increasing the length of the surface that an arc must travel between the inner diameter portion 207, i.e., termination material 220b, and outer diameter portion 205, i.e., termination material 220a.

Figure 13:
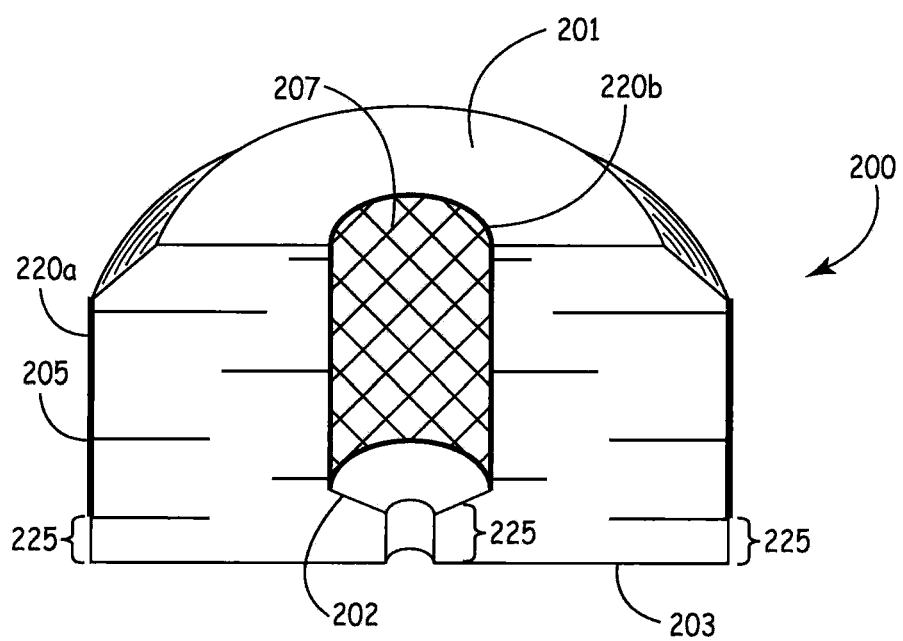

Similar to the capacitor illustrated in FIG. 12, FIG. 13 illustrates a capacitor 200 with unterminated portions 225 for inhibiting high voltage arcing along the bottom portion 203 of the capacitor. As shown in FIG. 13, capacitor 200 includes a tapered inner diameter portion 202 from which termination material 220b is absent. The absence of termination material 220b in tapered inner diameter portion 202 inhibits high voltage arcing along the bottom portion 203 of the capacitor 200, for example, by increasing the length of the surface that an arc must travel between the inner diameter portion 207, i.e., termination material 220b, and outer diameter portion 205, i.e., termination material 220a.

Figure 14:
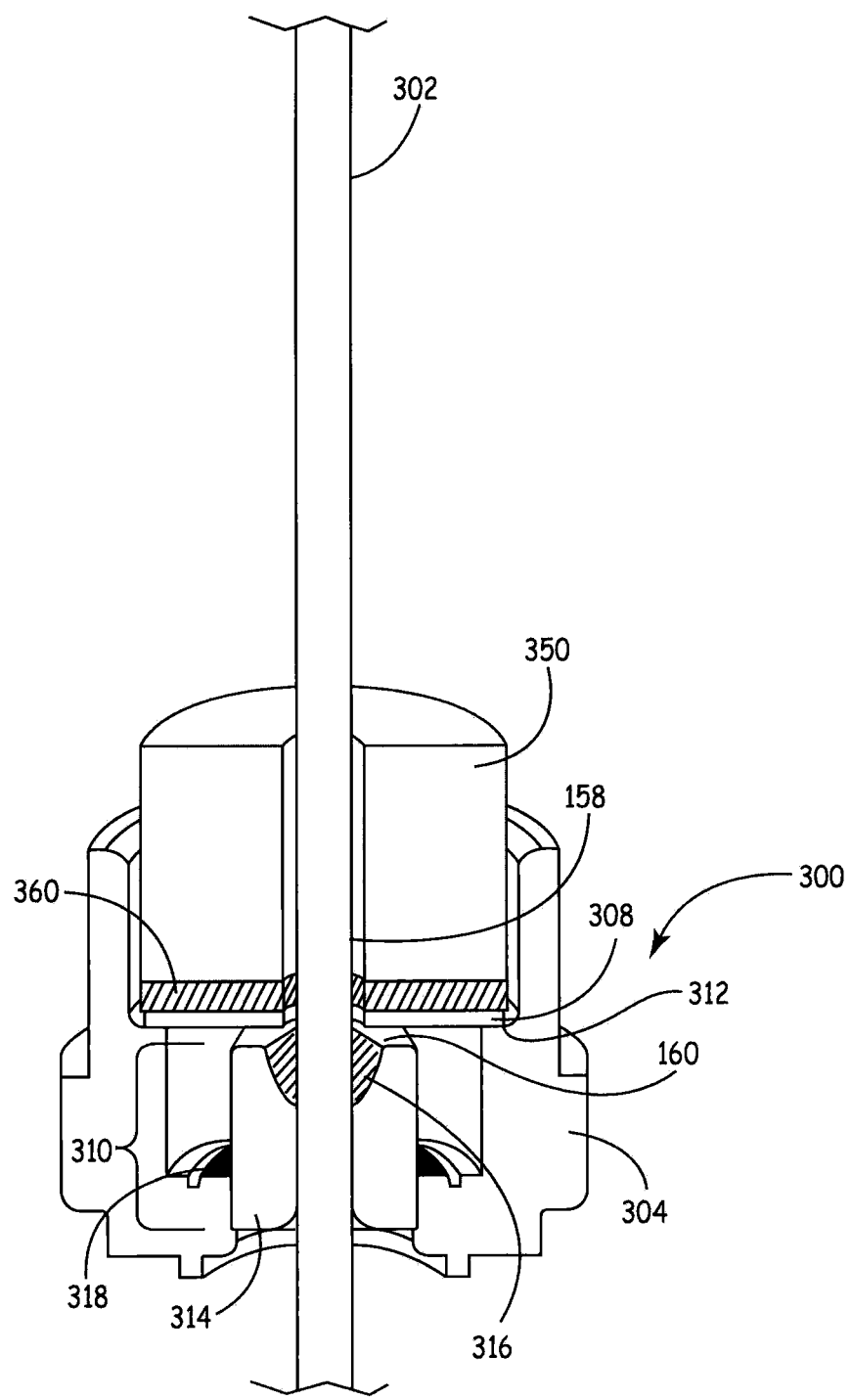
FIG. 14 is a cross-sectional view of a unipolar (single pin) filtered feedthrough assembly with an attached discrete discoidal capacitor that includes a fixedly attached insulative member according to various exemplary embodiments of the present disclosure.

Referring now to FIG. 14, a filtered feedthrough assembly 300 according to various exemplary embodiments of the present disclosure is illustrated. Filtered feedthrough assembly 300 is unipolar (single pin) and has a terminal pin 302 extending therethrough. Assembly 300 comprises a generally cylindrical ferrule 304 having a cavity through which pin 302 passes. Ferrule 304 is made of an electrically conductive material (e.g., titanium alloy) and is configured to be fixedly coupled (e.g., welded) to the container of a medical device as described below in conjunction with FIG. 19. An insulating structure comprising supporting structure 308 and a joint-insulator sub-assembly 310 is disposed within ferrule 304 to secure pin 302 relative to ferrule 304 and to electrically isolate pin 302 from ferrule 304. Both of the supporting structure 308 and a joint-insulator sub-assembly 310 are disposed around terminal pin 302. The joint-insulator sub-assembly 310 acts as an insulative seal and can take the form of, for example, a braze joint. Supporting structure 308 is made of a non-conductive material (e.g., polyimide, polyetheretherketone (PEEK) or similar material) and rests on an inner ledge 312 provided within ferrule 304. As will be seen, a discrete discoidal capacitor can be threaded over terminal pin 302 and fixedly coupled to supporting structure 308 to attach the capacitor to feedthrough assembly 300. Alternatively, the supporting structure 308 can be eliminated from the assembly and the discrete discoidal capacitor can rest on inner ledge 312 directly, as is described in U.S. patent application Ser. No. 12/183,922, filed Jul. 31, 2008, entitled "Novel Capacitive Elements And Filtered Feedthrough Assemblies For Implantable Medical Devices," U.S. patent application Ser. No. 12/183,940, filed Jul. 31, 2008, entitled "Novel Capacitive Elements And Filtered Feedthrough Assemblies For Implantable Medical Devices" and U.S. patent application Ser. No. 12/183,953, filed Jul. 31, 2008, entitled "Novel Capacitive Elements And Filtered Feedthrough Assemblies For Implantable Medical Devices," which are incorporated herein in their entirety.

Braze joint 310 comprises three main components: an insulator ring 314 (e.g., made from a ceramic material) that insulates pin 302 from ferrule 304, a pin-insulator braze 316 (e.g., made from gold) that couples insulating ring 314 to pin 302, and an insulator-ferrule braze 318 (e.g., made from gold) that couples insulating ring 314 to ferrule 304. Braze joint 310 is exposed along the underside of ferrule 304. When ferrule 304 is fixedly coupled to the container of the medical device, the lower portion of ferrule 304, and thus the lower portion of braze joint 310, can be exposed to body fluids. For this reason, it is important that braze joint 310 forms a hermetic seal between ferrule 304 and terminal pin 302, which can be leak tested, as described above.

Terminal pin 302 provides a conductive path from the interior of a medical device (not shown) to one or more lead wires exterior to the medical device. As described previously, these lead wires are known to act as antennae that collect stray electromagnetic interference (EMI) signals, which can interfere with the proper operation of the device. To suppress and/or transfer such EMI signals to the container of the medical device, a discrete discoidal capacitor 350 with fixedly attached insulative member 360 can be attached to feedthrough assembly 300. In particular, the capacitor 350 can be disposed around and electrically coupled to terminal pin 302 and fixedly coupled to supporting structure 308, described more fully below.

Figure 15:
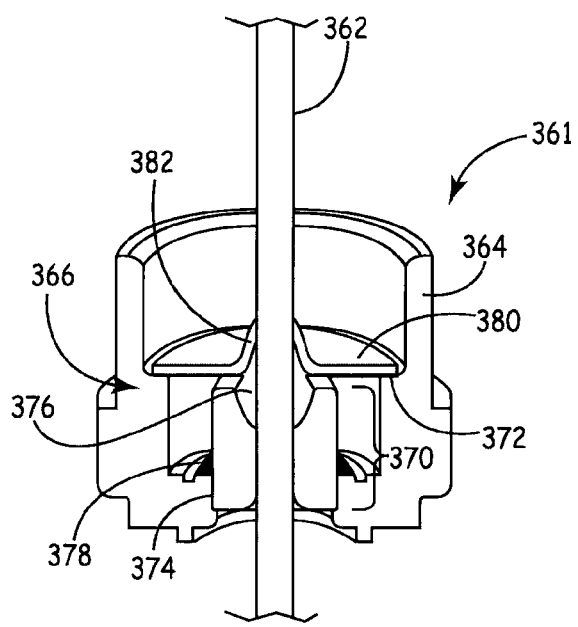
FIG. 15 is a cross-sectional view of a unipolar (single pin) filtered feedthrough assembly according to various exemplary embodiments of the present disclosure.
Figure 16:
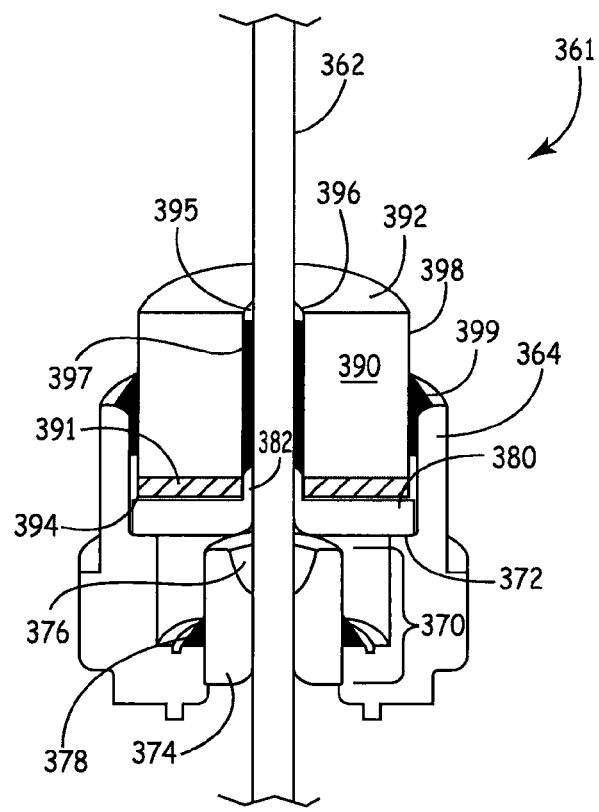
FIG. 16 is a cross-sectional view of a unipolar (single pin) filtered feedthrough assembly with an attached discrete discoidal capacitor that includes a fixedly attached insulative member according to various exemplary embodiments of the present disclosure.

Referring now to FIGS. 15-16, an alternative filtered feedthrough assembly 361 according to various exemplary embodiments of the present disclosure is illustrated. A support structure 380 is sized and configured to be received within ferrule 364. In the illustrated example, support structure rests upon an inner ledge 372 provided within ferrule 364. Support structure 380 can be designed for use in a unipolar, i.e., single pin, feedthrough assembly or a multipolar, i.e., multiple pin, feedthrough assembly. The design differences between a unipolar and multipolar support structure 380 are minor and essentially equate to including the correct number of openings within support structure 380 to accommodate the number of terminal pin(s) 362 in the feedthrough. The support structure 380 can be similar to those described in U.S. patent application Ser. No. 12/368,847, filed Feb. 10, 2009, entitled "Filtered Feedthrough Assembly And Associated Method," which is herein incorporated in its entirety.

The filtered feedthrough assembly 361 according to various exemplary embodiments can be assembled as follows. The joint-insulator sub-assembly 370 is disposed within ferrule 364 to secure pin 362 relative to ferrule 364 and to electrically isolate pin 362 from ferrule 364. Support structure 380 can then be inserted within ferrule 364 such that terminal pin 362 extends through the opening therein. The opening of support structure 380 can be sized so as to mate with terminal pin 362 in a secure fashion. A partially assembled filtered feedthrough assembly 361 according to various exemplary embodiments of the present disclosure is illustrated in FIG. 15.

Capacitor 390 with fixedly attached insulative member 391 is then inserted at least partially within the ferrule 364 such that terminal pin 362 extends through, and a projection 382 of support structure 380 is partially received within, aperture 395. In some exemplary embodiments, the projection 382 and aperture 395 are sized such that the projection 382 is tightly secured in the aperture 395, e.g., to create a seal between projection 382 and aperture 395. In this manner, support structure 380 can be physically coupled to capacitor 390 without the use of non-conductive epoxy or other compound as in the prior art, which not only simplifies the assembly process, but also prevents the intrusion of the non-conductive epoxy into the joint-insulator sub-assembly 370. Furthermore, projection 382 can be sized and positioned such that the terminal pin 362 is substantially centered within aperture 395, which will assist in the formation of a reliable electrical connection between capacitor 390 and terminal pin 362.

After placement of capacitor 390 within ferrule 364, the inner diameter portion 396 of capacitor 390 is electrically coupled to the terminal pin 362, e.g., by means of solder or conductive epoxy 397. Similarly, the outer diameter portion 398 of capacitor 390 is electrically coupled to the ferrule 364, e.g., by means of solder or conductive epoxy 399. Support structure 380, and specifically the coupling of aperture 395 and projection 382, inhibits or prevents the flow of solder or conductive epoxy 397, 399 into the joint-insulator sub-assembly 370. A fully assembled filtered feedthrough assembly 361 according to various exemplary embodiments of the present disclosure is illustrated in FIG. 16.

Figure 17:
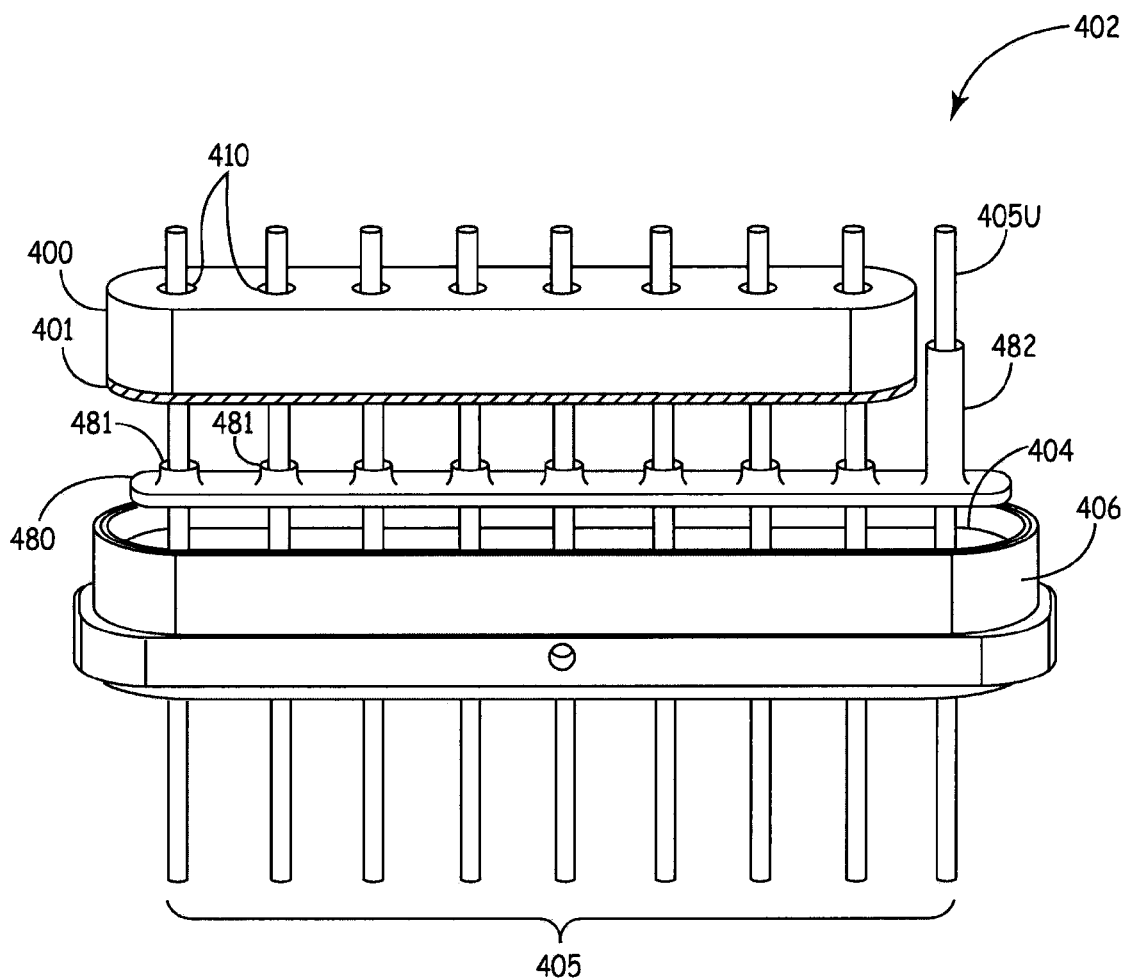
FIG. 17 is an exploded view of a multipolar (multiple pin) filtered feedthrough assembly illustrating the attachment of a monolithic discoidal capacitor that includes a fixedly attached insulative member in accordance with various exemplary embodiments of the present disclosure.

FIG. 17 illustrates the attachment of a monolithic discoidal capacitor 400, which has already been fixedly attached with insulative member 401 in one of the manners described above, to a multipolar feedthrough assembly 402 in accordance with various exemplary embodiments of the present invention. Filtered feedthrough assembly 402 comprises a ferrule 406 and an insulating structure 404 disposed within ferrule 406. Filtered feedthrough assembly 402 guides an array of terminal pins 405 through the container of a medical device to which ferrule 404 is coupled (shown in FIG. 19). As described above, terminal pin array 405 and the lead wires to which array 405 is coupled can act as an antenna and collect undesirable EMI signals. Monolithic discoidal capacitor 400 can be attached to feedthrough assembly 402 to provide EMI filtering. Capacitor 400 and insulative member 401 is provided with a plurality of terminal pin-receiving apertures 410 therethrough. Capacitor 400 with attached insulative member 401 is inserted over terminal pin array 405 such that each pin in array 405 is received by a different aperture 410 and placed in an abutting relationship with insulating structure 404. If desired, one terminal pin in array 405 can be left unfiltered as shown in FIG. 17 to serve as an RF antenna. Support structure 480 is provided between insulating structure 404 and capacitor 400 and insulative member 401. Capacitor 400 and insulative member 401 can be coupled to support structure 480, such as by projections 481 on support structure 480 being securely received within terminal pin-receiving apertures 410, similarly to that discussed above in U.S. patent application Ser. No. 12/368,847. Furthermore, a sleeve 482 can be included on support structure 480 to assist in the isolation of the unfiltered pin 405U from capacitor 400.

FIG. 18 is an exploded view of an implantable medical device (e.g., a pulse generator) 450 coupled to a connector block 451 and a lead 452 by way of an extension 454. The proximal portion of extension 454 comprises a connector 456 configured to be received or plugged into connector block 451, and the distal end of extension 454 likewise comprises a connector 458 including internal electrical contacts 460 configured to receive the proximal end of lead 452 having electrical contacts 462 thereon. The distal end of lead 452 includes distal electrodes 464, which can deliver electrical pulses to target areas in a patient's body (or sense signals generated in the patient's body, e.g., cardiac signals).

After a capacitor 400 and insulative member 401 have been attached to feedthrough assembly 402 in the manner described above, assembly 402 can be welded to the housing of an implantable medical device 450 as shown in FIG. 19. Medical device 450 comprises a container 452 (e.g. titanium or other biocompatible material) having an aperture 454 therein through which feedthrough assembly 402 is disposed. As can be seen, each terminal pin in array 405 has been trimmed and is electrically connected to circuitry 456 of device 450 via a plurality of connective wires 458 (e.g., gold), which can be coupled to terminal pin array 405 by wire bonding, laser ribbon bonding, or the like. After installation, feedthrough assembly 402 and capacitor 400 collectively function to permit the transmission of relatively low frequency electrical signals along the terminal pins in array 405 to circuitry 456 while shunting undesired high frequency EMI signals to container 452 of device 450.

The broad teachings of the disclosure can be implemented in a variety of forms. Therefore, while this disclosure includes particular examples, the true scope of the disclosure should not be so limited since other modifications will become apparent upon a study of the drawings, the specification, and the following claims.

What is claimed is:

1. A method of assembling a filtered feedthrough assembly, comprising:
    providing a capacitor having a top portion, a bottom portion, an outer diameter portion and an inner diameter portion, wherein the inner diameter portion defines at least one aperture extending from the top portion to the bottom portion;
    fixedly attaching an insulative member to the bottom portion of the capacitor, the insulative member substantially covers the bottom portion of the capacitor by extending around a radius from the inner diameter portion into contact with the outer diameter portion of the capacitor to inhibit high voltage surface arcing; and
    threading the capacitor and the insulative member over a terminal pin onto a supporting structure to couple the capacitor to the feedthrough assembly.

2. The method of claim 1, wherein the insulative member comprises a base member and an adhesive, the base member fixedly attached to the bottom portion of the capacitor by the adhesive.

3. The method of claim 2, wherein the base member comprises an alumina material, a plastic material, a polyimide material, a glass material, a ceramic material or a combination thereof.

4. The method of claim 2, wherein the adhesive comprises a glass material, a polyimide material or a combination thereof.

5. The method of claim 1, wherein the insulative member comprises an insulative coating adhered to the bottom portion of the capacitor.

6. The method of claim 1, wherein the insulative member comprises a low temperature co-fired ceramic material, the insulative member laminated to the bottom portion of the capacitor.

7. The method of claim 1 wherein the insulative member inhibits high voltage surface arcing along the bottom portion of the capacitor.

8. The method of claim 7 further comprising increasing a length of a surface that an arc travels between the inner diameter portion and the outer diameter portion of the capacitor.

9. The method of claim 8 further comprising preventing a direct line of sight between the terminal pin and the ferrule.

10. A method of claim 1 wherein the insulative member being attached to the capacitor without use of non-conductive epoxy.

11. A method of claim 1 wherein the base member comprising a plastic material.

12. A method of assembling a filtered feedthrough assembly, comprising:
    providing a capacitor having a top portion, a bottom portion, an outer diameter portion and an inner diameter portion, the capacitor including a plurality of conductive plates, wherein:
        the inner diameter portion defines at least one aperture extending from the top portion to the bottom portion;
        an outer diameter termination material on the outer diameter portion of the capacitor electrically couples a first subset of the plurality of conductive plates, the outer diameter termination material being absent from an outer diameter lower portion of the outer diameter portion adjacent the bottom portion of the capacitor; and
        an inner diameter termination material applied to the inner diameter portion of the capacitor, the inner diameter termination material electrically coupling a second subset of the plurality of conductive plates, the inner diameter termination material being absent from an inner diameter lower portion of the inner diameter portion adjacent the bottom portion of the capacitor
    inserting at least one terminal pin within a ferrule; and
    fixedly securing the capacitor within the ferrule, wherein the at least one terminal pin extends through the opening and extends through the at least one aperture,
    wherein the capacitor includes an insulative member fixedly attached to the bottom portion of the capacitor, the insulative member configured to inhibit high voltage arcing,
    wherein the insulative member extends from the inner diameter portion into contact with the outer diameter portion of the capacitor.

13. The method of claim 12, wherein the inner diameter lower portion and outer diameter lower portion comprise an insulative member fixedly attached to the bottom portion of the capacitor.

14. A method of assembling a filtered feedthrough assembly, consisting of:
    providing a capacitor having a top portion, a bottom portion, an outer diameter portion and an inner diameter portion, wherein the inner diameter portion defines at least one aperture extending from the top portion to the bottom portion;
    fixedly attaching an insulative member to the bottom portion of the capacitor, the insulative member configured to inhibit high voltage surface arcing;
    inserting at least one terminal pin within a ferrule;
    fixedly securing the capacitor with attached insulative member within the ferrule, wherein the at least one terminal pin extends through the opening and extends through the at least one aperture; and
    wherein the insulative member extends around a radius from the inner diameter portion into contact with the outer diameter portion of the capacitor, the insulative member inhibits high voltage arcing along the bottom portion of the capacitor by increasing a length of a surface that an arc must travel between an inner diameter portion and an outer diameter portion.

15. A method of claim 14 wherein the insulative member further configured to prevent a direct line of sight between the at least one terminal pin and the ferrule.

16. A method of assembling a filtered feedthrough assembly, consisting of:
    providing a capacitor having a top portion, a bottom portion, an outer diameter portion and an inner diameter portion, wherein the inner diameter portion defines at least one aperture extending from the top portion to the bottom portion;
    fixedly attaching an insulative member to the bottom portion of the capacitor, the insulative member configured to inhibit high voltage surface arcing;
    inserting at least one terminal pin within a ferrule; and
    fixedly securing the capacitor with attached insulative member within the ferrule, wherein the at least one terminal pin extends through the opening and extends through the at least one aperture;
    wherein the insulative member substantially covers the bottom portion of the capacitor, threading the capacitor and the insulative member over a terminal pin onto a supporting structure to attach the capacitor to a feedthrough assembly without use of non-conductive epoxy.

17. A method of assembling a filtered feedthrough assembly, comprising:
providing a capacitor having a top portion, a bottom portion, an outer diameter portion and an inner diameter portion, wherein the inner diameter portion defines at least one aperture extending from the top portion to the bottom portion;
fixedly attaching an insulative member to the bottom portion of the capacitor, the insulative member substantially covers the bottom portion of the capacitor by extending around a radius from the inner diameter portion into contact with the outer diameter portion of the capacitor to inhibit high voltage surface arcing; and
threading the capacitor and the insulative member over a terminal pin onto a supporting structure to couple the capacitor to the feedthrough assembly without curing a preform.

* * * * *